US006566473B1

(12) United States Patent
Prettypaul et al.

(10) Patent No.: US 6,566,473 B1
(45) Date of Patent: May 20, 2003

(54) PROCESS FOR MAKING A VINYL AMIDE POLYMER COMPOSITION FOR SKIN AND HAIR COMPOSITIONS

(75) Inventors: Donald I. Prettypaul, Englewood, NJ (US); Jenn S. Shih, Paramus, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/300,124

(22) Filed: Nov. 20, 2002

(51) Int. Cl.$^7$ ................................................. C08F 26/08
(52) U.S. Cl. ........................ 526/264; 526/194; 526/210; 526/219.6; 526/232.1; 526/236; 526/307.1; 526/307.3; 526/307.5; 526/317.1; 526/318.3; 526/320; 526/328.5
(58) Field of Search ................................. 526/194, 210, 526/219.6, 232.1, 236, 264, 307.1, 307.3, 307.5, 317.1, 318.3, 320, 328.5

(56) References Cited

U.S. PATENT DOCUMENTS

| 6,048,522 A | * | 4/2000 | Plochocka et al. | ....... | 427/78.24 |
| 6,177,068 B1 | * | 1/2001 | Shih et al. | ................ | 424/70.17 |
| 6,255,421 B1 | * | 7/2001 | Plochocka et al. | .......... | 526/194 |
| 6,300,442 B1 | * | 10/2001 | Plochocka | .................. | 526/194 |

* cited by examiner

*Primary Examiner*—Helen L. Pezzuto
(74) *Attorney, Agent, or Firm*—Walter Katz; William J. Davis; Marilyn J. Maue

(57) ABSTRACT

A non-aqueous, heterogeneous polymerization process comprises heating a reaction mixture of about 5–70%, preferably 10–50%, by weight, of a vinyl amide monomer in an oil as solvent, and a water-soluble cosolvent, and a free radical initiator, optionally in the presence of a crosslinking agent and/or a surfactant, wherein the oil solvent is present in an amount sufficient to keep the resultant polymer in a stirrable state throughout the polymerization. The polymer reaction product is capable of forming a uniform emulsion or gel upon addition of water thereto.

16 Claims, No Drawings

PROCESS FOR MAKING A VINYL AMIDE POLYMER COMPOSITION FOR SKIN AND HAIR COMPOSITIONS

BACKGROUND OF THE INVENTION

1. Field of the Invention

This invention relates to a polymerization process, and more particularly, to non-aqueous, heterogeneous polymerization of a vinyl amide monomer in oil as a solvent and including a water-soluble cosolvent.

2. Description of the Prior Art

J. Shih, in U.S. Pat. Nos. 6,255,421; 6,255,422 and 6,300,442; described a non-aqueous, heterogeneous polymerization process for making vinyl polymers using an oil solvent, whose presence both during the polymerization and in the reaction product is advantageous for commercial use of the vinyl polymer, particularly in cosmetic compositions.

Accordingly, in this invention, it is desired to provide a new and improved non-aqueous, polymerization process to increase the stability of a polymer/oil-cosolvent solution.

These and other objects and features of the invention will be made apparent from the following description of the invention.

SUMMARY OF THE INVENTION

What is described herein is a non-aqueous, heterogeneous polymerization process for making vinyl amide polymers. The process comprises heating a reaction mixture of, by weight, about 5–70%, preferably 10–50% of a vinyl amide monomer in an oil as solvent, and including a water-soluble cosolvent, and a free radical initiator, optionally in the presence of a crosslinking agent and/or a surfactant, wherein the oil solvent is present in an amount sufficient to keep the resultant polymer in a stable stirrable state throughout the polymerization. The polymer reaction product obtained thereby is capable of forming a uniform emulsion or gel upon addition of water thereto.

DETAILED DESCRIPTION OF THE INVENTION

The unique properties of many oils make it desirable to include them in aqueous-based compositions. For example, cosmetically and pharmaceutically-acceptable materials such as silicone oils, fluids and gums, mineral oils, and water-insoluble organic esters such as isopropyl palmitate and isopropyl myristate, are particularly useful in formulations for the hair and skin. In these compositions, the lubricity and hydrophobicity properties of the oils are beneficial for the user.

In this invention, vinyl polymers useful in cosmetic compositions are prepared in a non-aqueous, heterogeneous polymerization process using both an oil as a solvent and a water-soluble cosolvent, for the monomer during the polymerization reaction. The oil solvent and water-soluble cosolvent also acts as a medium to keep the polymer product in a stirrable state throughout the polymerization. The reaction product is a slurry of the vinyl polymer in oil. If desired, the reaction product may be filtered to provide the vinyl polymer as a powder swollen with oil. Thereafter, the reaction product itself, or the polymer powder swollen with oil and cosolvent, may be homogenized with water to form a uniform liquid emulsion or gel which is directly useful as the cosmetic or pharmaceutical composition.

Generally about 5–70%, preferably 10–50%, by weight, of the vinyl monomer reactant is used in the process, and about 30–95% of the oil and cosolvent is included for the solvent and medium functions in the process.

Suitable oils for use herein include cosmetically or pharmaceutically-acceptable materials, such as silicone oils, fluids and gums, mineral oils and water-insoluble organic esters such as diisopropyl adipate, isopropyl palmitate, isocetyl stearate and isopropyl myristate.

Suitable silicone oils or fluids for use in the invention may be selected from non-volatile silicones, such as polyalkyl siloxanes, polyaryl siloxanes, polyalkylaryl siloxanes and polyether siloxane copolymers; and volatile silicones such as cyclomethicones also may be used.

Non-volatile polyalkylsiloxanes thus include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cS, and most preferably, a viscosity of up to about 15,000 cS.

Suitable non-volatile polyalkylaryl siloxanes include, for example, poly(methylphenyl) siloxanes having viscosities of about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenylsiloxane) copolymers having a viscosity in the range of about 10 to 100,000 cS at 25° C. are useful.

These and other suitable silicones are disclosed in U.S. Pat. Nos. 2,826,551, 3,964,500 and 4,364,837.

The cosolvent included in the process is a water soluble compound, preferably a glycol, e.g. 2-methyl-2,4-pentanediol, 1,4-hexanediol and 1,6-hexanediol. The function of the cosolvent is to stabilize the polymer/oil emulsion to a level not ordinarily obtained without the cosolvent present.

The polymerization process is carried out with a free radical initiator present in the polymerization reaction mixture. The reaction product thus includes the vinyl polymer corresponding to the vinyl monomer or monomers selected. Suitable free radical initiators are diacetyl peroxide, dibenzoyl peroxide, dilauroyl peroxide, t-butyl peroxypivalate, t-butyl peroctoate, t-amyl peroxypivalate, t-butyl peroxy-2-ethylhexanoate, di-(4-t-butylcyclohexyl) peroxydicarbonate, 2,2'-azo-bis(isobutyronitrile), 2,2'-azo-bis(2,4-dimethylvaleronitrile), or 1,1'-azo-bis(cyanocyclohexane), and mixtures thereof.

A crosslinked vinyl amide polymer may be obtained in the process when the optional crosslinking agent is included in the reaction mixture. Suitably, the crosslinking agent is present in an amount of about 0.1–10 wt. %, preferably 0.3–3%, based on the amount of vinyl monomer present. In the presence of such a crosslinking agent, the vinyl monomer will form the corresponding crosslinked vinyl polymer, which, upon homogenization with water, will provide a uniform liquid gel product.

In the practice of the present invention, the oil and cosolvent is charged into a reactor, under agitation, and in a nitrogen atmosphere, and heated to about 40°–150° C., preferably about 65° C. Then the free radical initiator of 0.1–10%, preferably 0.2–5%, is added. Thereafter the vinyl monomer is added continuously over a period of about 1–12 hours, preferably about 3–6 hours. Preferably, the vinyl monomer and optional crosslinking agent are fed into the reactor at a rate such that substantially no free monomer is present during the polymerization.

After polymerization is complete, the polymer is obtained as a slurry in oil and cosolvent. The slurry can be used as is or filtered to remove excess oil and cosolvent where the product consists of solid polymer with significant amount of absorbed oil. Both slurry and filtered polymer are useful in cosmetic and pharmaceutical formulations.

Suitable vinyl amide monomers include, but are not limited to, and N-vinyl lactams, such as N-vinylpyrrolidone, N-vinylcaprolactam; as well as non-ring vinylamides as N-vinylformamide; optionally with one or more comonomers such as vinyl acetate, acrylic acid, methacrylic acid, acrylamide, methacrylamide, an alkyl(meth)acrylate, an alkyl(meth)acrylamide, a hydroxyalkyl(meth)acrylate and a hydroxyalkyl(meth)acrylamide, and a N,N-dialkylaminoalkyl(meth)acrylate wherein alkyl is independently a $C_1$ to $C_4$ alkyl group and N,N-dialkylaminoalkyl methacrylamide (alkyl being as defined before), and their quaternary derivatives; and mixtures thereof.

Suitable crosslinking agents include, but are not limited to, diallylimidazolidone, divinyl ether of diethylene glycol, pentaerythritol triallyl ether (PETE); pentaerythritol triacrylate (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis(methacrylamide), methylene-bis(acrylamide), N,N-divinylimidazolidone, ethylidene-bis(N-vinyl-pyrrolidone) (EBVP), hexaallyl sucrose, or bis(N,N-acrylamide).

Another optional component of the reaction mixture is a surfactant. The presence of a surfactant will function to effectively stabilize the desired emulsion and gel products. Generally, an oil soluble surfactant is present in the reaction mixture and a water soluble surfactant during the water homogenization, in an amount of about 0.5–10%, preferably 1–5%, based on oil present. Suitable oil soluble surfactants useful for polymerization include, but are not limited to, cetyl dimethicone copolyol (Abil® EM-90, product of Goldschmidt Chemical Corp.); Span® 80 (ICI) and Dow Corning 3225 silicone.

The resultant solutions have a solids content of about 5–70%, preferably 10–50%.

The products made herein may be easily converted into emulsions or emulsified hydrogels which contain the polymer (linear or crosslinked) in the aqueous phase.

The oil phase consists of the oil used during polymerization. The emulsions can be a water-in-oil (w/o), oil-in-water (o/w), or mixed type (w/o/w). When the polymer is crosslinked, the aqueous phase has attributes of a swollen crosslinked hydrogel. The hydrogel phase can be either dispersed in oil as fine gel particles (w/o), or the oil droplets can be dispersed in a continuous hydrogel phase (o/w).

The selected ratios of oil-to-water in such emulsions and emulsified hydrogels are predetermined by the desired use compositions; these can be adjusted within a broad range. Typically, oil-to-water ratios reside in the range of about 30:70 to about 10:90 by volume in the case of o/w emulsions and emulsified hydrogels. In corresponding w/o systems, the ratios of oil-to-water are suitably in the range of about 90:10 to about 30:70 by volume. Typically, when there is a need for a significant amount of oil in the final emulsion, the reaction product, that is, the slurry of polymer in oil, is directly converted into an emulsion or an emulsified hydrogel by addition of a calculated amount of water. When, however, the ratio of oil-to-water in the emulsion is desired to be low, the emulsion is made using the filtered reaction product that consists of polymer powder swollen with the absorbed oil.

When an o/w system is desired, the reaction product is gradually added to water, whereas when a w/o system is desired, water is added gradually to the reaction product, with appropriate rapid agitation or homogenization. Suitable surfactants should be added to these systems, such as, for example, Tween® 20, 21, 40, 61 (ICI) or Igepal® CO-630 (product of Rhone-Poulenc), for o/w emulsions and emulsified hydrogels; and Span® 60, 65, 80, 85 (ICI) for w/o systems. The surfactant added optionally to the polymerization reaction mixture also may be sufficient to form the desired emulsion or emulsified hydrogel.

The invention will now be described in further detail with reference to the following working examples.

EXAMPLE 1

Preparation of Surfactant-Free, Stable Oil Solution of Crosslinked PVP/AA

Into a 1-liter, 4-necked glass kettle, equipped two feeding pumps, an anchor agitator, a thermocouple and a condenser, was charged 540 g of isocetyl stearate and 60 g of 2-methyl-2,4-pentanediol as cosolvent. The solution was purged with nitrogen throughout the process. The solution was heated to 65° C. and held for 30 minutes. A feeding solution I was prepared by mixing 116 g of N-vinylpyrrolidone (VP) and 3.5 g of pentaerythritol triallyl ether (PETE). Feeding solution II comprised 116 g of acrylic acid (AA). 0.5 g of t-butylperoxypivalate was added to the kettle. Spontaneously feeding solutions I (VP and PETE) and II (AA) were pumped into kettle over 4 hours at a constant feeding rate. The solution was held at 65° C. for 1 hour and then raised to 90° C. 0.2 g of t-butylperoxypivalate was added every 2 hours for 5 times and the reactants held for 2 more hours after charging of the last increment of t-butylperoxypivalate. Then 2.0 g of DI water was added to hydrolyze any residual VP to <100 ppm, and the solution was stirred for 5 hours at 100° C. Cooled and discharged the solution and then homogenized the solution.

Solution Viscosity of Example 1

3.5 g of the solution of Example 1 was measured into a 4 oz. Jar and 0.5 g of triethanolamine and 96 g DI water were added. The solution was stirred at room temperature. A gel solution formed whose Brookfield viscosity was 80,000 cps.

EXAMPLE 2

Crosslinked (VP/AA/SMA)

Feeding Solution I: by mixing 140 g of N-vinylpyrrolidone (VP), 35 g of stearyl methacrylate (SMA) and 1.2 g of pentaerythritol triallylether (PETE).

Feeding Solution II: 59 g of acrylic acid (AA).

Example 1 was repeated to provide similar results with the above monomers.

To 7.5 g of the polymer solution was added 0.52 g of 2-amino-2-methylpropanol (AMP) and 91.98 g water. The solution was mixed with agitation. The gel formed within 5 minutes. The gel had a Brookfield viscosity of 50,000 cps. The gel showed a 85–90% curl retention on hair at 90% relative humidity chamber at 80° F. for 4 hours.

EXAMPLE 3

Crosslinked (VP/AA/DMAPMA)

Feeding Solution I: by mixing 160 g of N-vinylpyrrolidone (VP), 40 g of N,N-dimethylaminopropyl methacrylamide (DMAPMA) and 2.0 g of pentaerythritol triallylether (PETE).

Feeding Solution II: 7 g of acrylic acid (AA).

Example 1 was repeated to provide similar results with the above monomers.

EXAMPLE 4

Poly(VP/AA/SMA)

Into a 1-liter, 4-necked glass kettle, equipped with two feeding pumps, an anchor agitator, a thermocouple and a condenser, was charged 220 g of isocetyl stearate, 200 g of diisopropyl adipate and 40 g of 2-methyl-2,4-pentanediol. The solution was purged with nitrogen throughout the process. Heat the solution to 65° C. and held for 30 minutes. Prepared Feeding Solution I by mixing 150 g of N-vinylpyrrolidone (VP) and 40 g of stearyl methacrylate (SMA). Prepared Feeding Solution II with 60 g of acrylic acid (AA). Added 0.5 g of t-butylperoxypivalate and started spontaneously pumping Feeding Solutions I (VP and SMA) and II (AA) into kettle over 4 hours at a constant feeding rate. Held the solution at 65° C. for 1 hour and then raised the temperature to 90° C. Added 0.2 g of t-butylperoxypivalate every 2 hours for 5 times and held for another 2 hours after charging the last increment of t-butylperoxypivalate. Added 2.0 g of DI water and stirred for 5 hours at 100° C. Cooled and discharged the homogenized solution.

While the invention has been described with particular reference to certain embodiments thereof, it will be understood that changes and modifications may be made which are within the skill of the art. Accordingly, it is intended to be bound only by the following claims, in which:

What is claimed is:

1. A non-aqueous, heterogeneous polymerization process which provides a cosmetically or pharmaceutically-acceptable polymer swollen with an oil composition which comprises: polymerizing, by weight, about 5–70% of a vinyl amide monomer, optionally with a comonomer, in a total amount of about 30–95% of an oil as solvent and a water-soluble cosolvent, and a free radical initiator, optionally in the presence of a crosslinking agent and/or an oil soluble surfactant, with agitation, under an inert gas, at about 40–150° C., wherein said amount of the oil and cosolvent is sufficient to keep the resultant vinyl lactam polymer in a stirrable state until the end of the polymerization and wherein the vinyl monomer and optional crosslinking agent are fed into the reactor charged with said oil and cosolvent and free radical initiator continuously over a period of about 3–6 hours at a rate such that substantially no free monomer is present during the polymerization.

2. A process according to claim 1 wherein the oil is a silicone oil, a water-insoluble organic ester or a mineral oil.

3. A process according to claim 2 wherein the water-insoluble organic ester is diisopropyl adipate, isopropyl palmitate, isocetyl stearate or isopropyl myristate.

4. A process according to claim 1 wherein the water-soluble cosolvent is a glycol.

5. A process according to claim 4 wherein said glycol is propylene glycol, 1,6-hexane glycol, 1,4-hexane glycol, or 2-methyl-2,4-pentanediol.

6. A process according to claim 1 wherein said oil is present in an amount of 29–65% and said water-soluble cosolvent is 1–30%, by weight, of the total solvent.

7. A process according to claim 6 wherein said amounts are 40–60% and 5–15%, respectively.

8. A process according to claim 1 in which the oil soluble surfactant is present.

9. A process according to claim 1 which includes about 0.1–10 wt. % of a crosslinking agent, based on the amount of vinyl amide monomer present.

10. A process according to claim 9 wherein said crosslinking agent is present in an amount of 0.3–3%.

11. A process according to claim 1 wherein the vinyl amide monomer is N-vinylpyrrolidone or N-vinyl caprolactam.

12. A process according to claim 1 wherein the crosslinking agent is diallylimidazolidone, divinyl ether of diethylene glycol, pentaerythritol triallyl ether (PETE); pentaerythritol triacrylate (PETA), triallyl-1,3,5-triazine-2,4,6-(1H,3H,5H) trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis(methacrylamide), methylene-bis(acrylamide), N,N-divinylimidazolidone, ethylidene-bis(N-vinyl-pyrrolidone) (EBVP), hexaallyl sucrose, or bis(N,N-acrylamide).

13. A process according to claim 12 wherein the vinyl amide monomer is N-vinylpyrrolidone.

14. A process according to claim 1 wherein the free radical initiator is diacetyl peroxide, dibenzoyl peroxide, dilauroyl peroxide, t-butyl peroxypivalate, t-amyl peroxypivalate, t-butyl peroxy-2-ethyl-hexanoate; di-(4-tert-butylcyclohexyl)peroxydicarbonate, 2,2'-azo-bis (isobutyrolnitrile), 2,2'-azo-bis(2,4-dimethylvaleronitrile), or 1,1'-azo-bis(cyanocyclo-hexane), and mixtures thereof.

15. A process according to claim 1 wherein a small amount of water is added at the end of the process to reduce residual monomer level to below 100 ppm.

16. A process according to claim 1 wherein the comonomer is selected from vinyl acetate, acrylic acid, methacrylic acid, acrylamide, methacrylamide, an alkyl(meth)acrylate, an alkyl(meth)acrylamide, a hydroxyalkyl(meth)acrylate and a hydroxyalkyl(meth)acrylamide; and a N,N-dialkylaminoalkyl(meth)acrylate and a N,N-dialkylaminoalkyl methacrylamide wherein alkyl is independently a $C_1$ to $C_4$ alkyl group, and N-quaternary derivatives thereof.

* * * * *